US011511099B2

(12) United States Patent
Wijesuriya et al.

(10) Patent No.: US 11,511,099 B2
(45) Date of Patent: Nov. 29, 2022

(54) APPARATUS FOR DETECTING MATING OF A CAP WITH A FLUID DELIVERY DEVICE AND METHOD

(71) Applicant: Medtronic MiniMed, Inc., Northridge, CA (US)

(72) Inventors: Amith Wijesuriya, Los Angeles, CA (US); Thomas P. Miller, Porter Ranch, CA (US)

(73) Assignee: Medtronic MiniMed, Inc., Northridge, CA (US)

( * ) Notice: Subject to any disclaimer, the term of this patent is extended or adjusted under 35 U.S.C. 154(b) by 239 days.

(21) Appl. No.: 16/596,542

(22) Filed: Oct. 8, 2019

(65) Prior Publication Data

US 2021/0100996 A1 Apr. 8, 2021

(51) Int. Cl.
*A61M 39/10* (2006.01)
*A61M 39/02* (2006.01)
*A61M 5/168* (2006.01)
*A61M 5/145* (2006.01)

(52) U.S. Cl.
CPC ........ *A61M 39/1011* (2013.01); *A61M 5/145* (2013.01); *A61M 5/16831* (2013.01); *A61M 39/0247* (2013.01); *A61B 2562/0247* (2013.01); *A61M 2005/14506* (2013.01); *A61M 2039/1005* (2013.01)

(58) Field of Classification Search
CPC .... A61M 5/14244; A61M 5/145; A61M 5/28; A61M 5/281; A61M 2005/14506; A61M 2005/2411; A61M 2005/2433–2444; A61M 2005/2485; A61M 2005/2488; A61M 2005/2492; A61M 39/10; A61M 39/1011; A61M 39/12; A61M 2039/1005; A61M 2039/1044; A61M 2205/14; A61M 2205/332; A61M 2205/3331; A61M 2205/502; A61M 2205/52; A61M 2205/6036; B65D 51/248; B65D 55/00; B65D 55/028; B65D 55/04; B65D 55/12; B65D 2251/01; B65D 2585/56
See application file for complete search history.

(56) References Cited

U.S. PATENT DOCUMENTS

| | | |
|---|---|---|
| 4,755,173 A | 7/1988 | Konopka et al. |
| 5,391,250 A | 2/1995 | Cheney, II et al. |
| 5,485,408 A | 1/1996 | Blomquist |
| 5,522,803 A | 6/1996 | Teissen-Simony |
| 5,665,065 A | 9/1997 | Colman et al. |
| 5,800,420 A | 9/1998 | Gross et al. |
| 5,807,375 A | 9/1998 | Gross et al. |
| 5,925,021 A | 7/1999 | Castellano et al. |

(Continued)

*Primary Examiner* — Kami A Bosworth
(74) *Attorney, Agent, or Firm* — Keith D. Grzelak; Wells St. John P.S.

(57) ABSTRACT

An apparatus is provided for detecting mating of a cap with a fluid delivery device having a housing, a receptacle, and a sensor. The housing is configured to carry an insulin delivery device having a reservoir of the fluid. The receptacle is provided by the housing having a coupling with a locking recess configured to receive a cap with a sprung locking arm. The pressure sensor is carried by the receptacle proximate the coupling and configured to detect engagement force of the sprung locking arm with the receptacle when mated with the housing. A method is also provided.

16 Claims, 5 Drawing Sheets

(56) References Cited

U.S. PATENT DOCUMENTS

| | | | |
|---|---|---|---|
| 5,954,643 A | 9/1999 | Van Antwerp et al. | |
| 6,017,328 A | 1/2000 | Fischell et al. | |
| 6,171,276 B1* | 1/2001 | Lippe | A61M 5/20 604/67 |
| 6,186,982 B1 | 2/2001 | Gross et al. | |
| 6,246,992 B1 | 6/2001 | Brown | |
| 6,248,067 B1 | 6/2001 | Causey, III et al. | |
| 6,248,093 B1 | 6/2001 | Moberg | |
| 6,355,021 B1 | 3/2002 | Nielsen et al. | |
| 6,379,301 B1 | 4/2002 | Worthington et al. | |
| 6,544,212 B2 | 4/2003 | Galley et al. | |
| 6,558,351 B1 | 5/2003 | Steil et al. | |
| 6,585,695 B1* | 7/2003 | Adair | A61M 5/162 604/183 |
| 6,591,876 B2 | 7/2003 | Safabash | |
| 6,641,533 B2 | 11/2003 | Causey, III et al. | |
| 6,736,797 B1 | 5/2004 | Larsen et al. | |
| 6,749,587 B2 | 6/2004 | Flaherty | |
| 6,766,183 B2 | 7/2004 | Walsh et al. | |
| 6,801,420 B2 | 10/2004 | Talbot et al. | |
| 6,804,544 B2 | 10/2004 | Van Antwerp et al. | |
| 7,003,336 B2 | 2/2006 | Holker et al. | |
| 7,029,444 B2 | 4/2006 | Shin et al. | |
| 7,066,909 B1 | 6/2006 | Peter et al. | |
| 7,137,964 B2 | 11/2006 | Flaherty | |
| 7,303,549 B2 | 12/2007 | Flaherty et al. | |
| 7,399,277 B2 | 7/2008 | Saidara et al. | |
| 7,442,186 B2 | 10/2008 | Blomquist | |
| 7,602,310 B2 | 10/2009 | Mann et al. | |
| 7,647,237 B2 | 1/2010 | Malave et al. | |
| 7,699,807 B2 | 4/2010 | Faust et al. | |
| 7,727,148 B2 | 6/2010 | Talbot et al. | |
| 7,785,313 B2 | 8/2010 | Mastrototaro | |
| 7,806,886 B2 | 10/2010 | Kanderian, Jr. et al. | |
| 7,819,843 B2 | 10/2010 | Mann et al. | |
| 7,828,764 B2 | 11/2010 | Moberg et al. | |
| 7,879,010 B2 | 2/2011 | Hunn et al. | |
| 7,890,295 B2 | 2/2011 | Shin et al. | |
| 7,892,206 B2 | 2/2011 | Moberg et al. | |
| 7,892,748 B2 | 2/2011 | Norrild et al. | |
| 7,901,394 B2 | 3/2011 | Ireland et al. | |
| 7,942,844 B2 | 5/2011 | Moberg et al. | |
| 7,946,985 B2 | 5/2011 | Mastrototaro et al. | |
| 7,955,305 B2 | 6/2011 | Moberg et al. | |
| 7,963,954 B2 | 6/2011 | Kavazov | |
| 7,977,112 B2 | 7/2011 | Burke et al. | |
| 7,979,259 B2 | 7/2011 | Brown | |
| 7,985,330 B2 | 7/2011 | Wang et al. | |
| 8,024,201 B2 | 9/2011 | Brown | |
| 8,100,852 B2 | 1/2012 | Moberg et al. | |
| 8,114,268 B2 | 2/2012 | Wang et al. | |
| 8,114,269 B2 | 2/2012 | Cooper et al. | |
| 8,137,314 B2 | 3/2012 | Mounce et al. | |
| 8,181,849 B2 | 5/2012 | Bazargan et al. | |
| 8,182,462 B2 | 5/2012 | Istoc et al. | |
| 8,192,395 B2 | 6/2012 | Estes et al. | |
| 8,195,265 B2 | 6/2012 | Goode, Jr. et al. | |
| 8,202,250 B2 | 6/2012 | Stutz, Jr. | |
| 8,207,859 B2 | 6/2012 | Enegren et al. | |
| 8,226,615 B2 | 7/2012 | Bikovsky | |
| 8,257,259 B2 | 9/2012 | Brauker et al. | |
| 8,267,921 B2 | 9/2012 | Yodfat et al. | |
| 8,275,437 B2 | 9/2012 | Brauker et al. | |
| 8,277,415 B2 | 10/2012 | Mounce et al. | |
| 8,292,849 B2 | 10/2012 | Bobroff et al. | |
| 8,298,172 B2 | 10/2012 | Nielsen et al. | |
| 8,303,572 B2 | 11/2012 | Adair et al. | |
| 8,305,580 B2 | 11/2012 | Aasmul | |
| 8,308,679 B2* | 11/2012 | Hanson | A61M 5/1413 604/67 |
| 8,313,433 B2 | 11/2012 | Cohen et al. | |
| 8,318,443 B2 | 11/2012 | Norrild et al. | |
| 8,323,250 B2 | 12/2012 | Chong et al. | |
| 8,343,092 B2 | 1/2013 | Rush et al. | |
| 8,352,011 B2 | 1/2013 | Van Antwerp et al. | |
| 8,353,829 B2 | 1/2013 | Say et al. | |
| 2006/0167414 A1* | 7/2006 | Scott | A61M 5/1456 604/152 |
| 2007/0123819 A1 | 5/2007 | Mernoe et al. | |
| 2010/0087778 A1* | 4/2010 | Genosar | A61M 5/14248 604/65 |
| 2010/0160861 A1 | 6/2010 | Causey, III et al. | |
| 2011/0257602 A1* | 10/2011 | Watanabe | A61M 7/0427 604/189 |
| 2016/0015885 A1* | 1/2016 | Pananen | A61M 5/1456 604/111 |
| 2016/0048657 A1* | 2/2016 | LeBrun | G16H 40/67 705/2 |
| 2020/0324047 A1* | 10/2020 | Beggs | A61M 5/16886 |

* cited by examiner

APPARATUS FOR DETECTING MATING OF A CAP WITH A FLUID DELIVERY DEVICE AND METHOD

CROSS REFERENCE TO RELATED APPLICATION

This application does not claim priority from any other application.

TECHNICAL FIELD

The subject matter of this application pertains to connections on infusion pumps. More particularly, the subject matter relates to a sensing apparatus on a housing of an infusion pump.

BACKGROUND OF THE DISCLOSURE

It is previously known to removably affix consumable caps and lines to infusion devices. The use of locking caps that are removably mated with a housing and a supply of fluid, such as insulin, are previously known. However, the ability to detect and monitor scheduled proper use of consumables is not known. Further, the ability to detect replacement and usage of compliant consumables has not been available.

SUMMARY

In one aspect, an apparatus is provided for detecting releasable coupling of a cap from a fluid delivery device. The apparatus includes a housing, a receptacle, an infusion cap, and a sensor. The housing is configured to carry a fluid delivery device having a reservoir of the fluid. The receptacle is provided by the housing having a coupling with an interface and a clip receiver. The infusion cap is coupled with a delivery tube and having a complementary coupling configured to engage with the interface of the receptacle coupling including a spring clip configured to interlock in urged engagement with the clip receiver during assembly. The pressure sensor is carried by the receptacle within the first connector interface and is configured to detect load transfer from the spring clip to the receptacle during mating and de-mating of the cap from the housing.

In another aspect, an apparatus is provided for detecting mating of a cap with a fluid delivery device having a housing, a receptacle, and a sensor. The housing is configured to carry a fluid delivery device having a reservoir of the fluid. The receptacle is provided by the housing having a coupling with a locking recess configured to receive a cap with a sprung locking arm. The pressure sensor is carried by the receptacle proximate the coupling and configured to detect engagement force of the sprung locking arm with the receptacle when mated with the housing.

In yet another aspect, a method is provided for detecting user mating/demating of a cap and a delivery tube with a fluid delivery device. The method includes: providing a housing supporting a reservoir of the fluid, having a receptacle, a cap with a delivery tube configured to removably mate with the receptacle, and a pair of mating interlocking connectors provided between the cap and the receptacle, the connector on the cap having a locking wing with a outwardly extending finger extending from a flexible arm that is urged inwardly when de-mating and mating the cap from the receptacle proximate a locked position; detecting a force from the urged flexible arm while engaging and disengaging the cap from the receptacle; and recording in the memory the detected force between the cap and the receptacle during mating and demating.

These and other aspects are contemplated and described herein. It will be appreciated that the foregoing summary sets out representative aspects of a system and method for detecting releasable coupling of a cap with a fluid delivery device and assists skilled readers in understanding the following detailed description.

BRIEF DESCRIPTION OF THE DRAWINGS

Exemplary embodiments of the various disclosures are described below with reference to the following accompanying drawings. The drawings may be considered to represent scale.

DETAILED DESCRIPTION OF THE EMBODIMENTS

This disclosure is submitted in furtherance of the constitutional purposes of the U.S. Patent Laws "to promote the progress of science and useful arts" (Article 1, Section 8).

As used herein, the term "spring clip" refers to any structurally articulating or urgeable component of a cap or a cap/housing assembly that engages in assembly to generate an assembly force capable of being detected using a sensor during assembly and/or when assembled together.

Figures 1, 2:
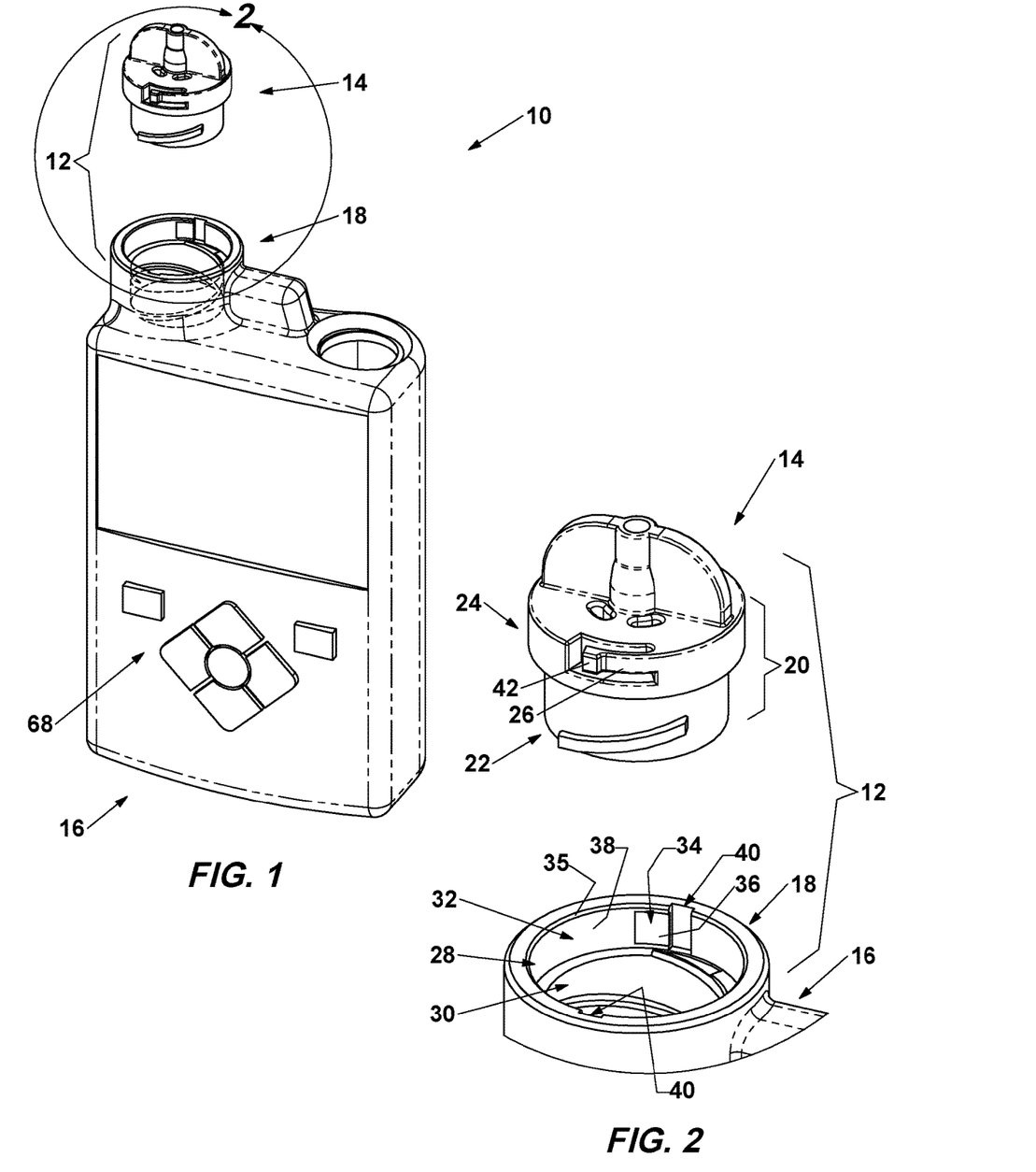
FIG. 1 is a perspective view from above of a housing and a cap removed from the housing for a fluid pump assembly.
FIG. 2 is an enlarged perspective view of the housing receptacle and the removed infusion cap.

FIG. 1 illustrates an infusion device 10 with a user interface 68 and having a connection interface 12 configured to removably attach a cap 14 with an infusion line (not shown) to a medication reservoir (not shown) within a housing 16. A receiver, or port 18 in housing 16 removably receives infusion cap 14 via connection interface, or connector assembly 12. Cap 14 forms part of a fluid infusion delivery system and housing 16 forms an encasement for the user interface 86, control system, fluid reservoir, piston (pump), motor, pump control circuitry, and power supply (battery). A fluid, such as insulin, is pumped from housing 16 through cap 14 and into a delivery tube (not shown).

FIG. 2 illustrates a sensor 36 carried in receiver 18 of housing 16 to detect engagement forces between cap 14 and receiver 18 as cap 14 is designed to apply pressure to an inner surface of receiver with a known pressure value or a unique pressure range for the cap 14 and receiver 18 combination. A detected pressure value can indicate how often cap 14 is removed and further detect a threshold load (within a design range) that can authenticate a cap by complying with a specific design range provided by a specific manufacturing source of cap 14. Cap 14, in use, is a consumable that is periodically replaced and housing 16 is reused repeatedly. Accordingly, sensor 36 is placed in a recess 34 of receptacle on housing 18 so it can be repeatedly used while caps 14 are consumed and replaced periodically. Such design saves cost because the sensing components on housing 16 get reused over a significantly larger period of time than if sensor 36 were placed on cap 14.

As shown in FIG. 2, connector 20 on cap 14 includes a lower, reduced diameter threaded portion 22 and an increased diameter locking body, or spring arm portion 24. Threaded portion 22 is cylindrical and includes a pair of opposed male thread segments (not numbered). Spring arm portion 24 includes a pair of wings, or spring arms 26 provided on opposites of a cylindrical wall portion of spring arm portion 24 terminating in radial outwardly extending ribs 42. A complementary pair of vertical slots 40 are forward radially outwardly of surface 38 such that corresponding terminal locking tabs 42 interlock in respective slots 40 to lock cap 14 within receiver 18. A female cylindrical locking surface 32 has a slightly larger diameter than a smaller cylindrical female threaded portion 30, which has a pair of opposed female thread segments (not numbered). Male threaded portion 22 mates with female threaded portion 30 while wing lock portion 24 engages helically within cylindrical surface 38 receiver 18 while spring arms 26 are urged radially inwardly until ribs 42 rotate into corresponding slots 40. Each rib 42 has a chamfered and beveled rearward edge so that rotation of cap 14 relative to receiver 18 will drive each rib 42 and spring arm 26 radially inwardly when removing cap 14 from receiver 18.

Figure 3:
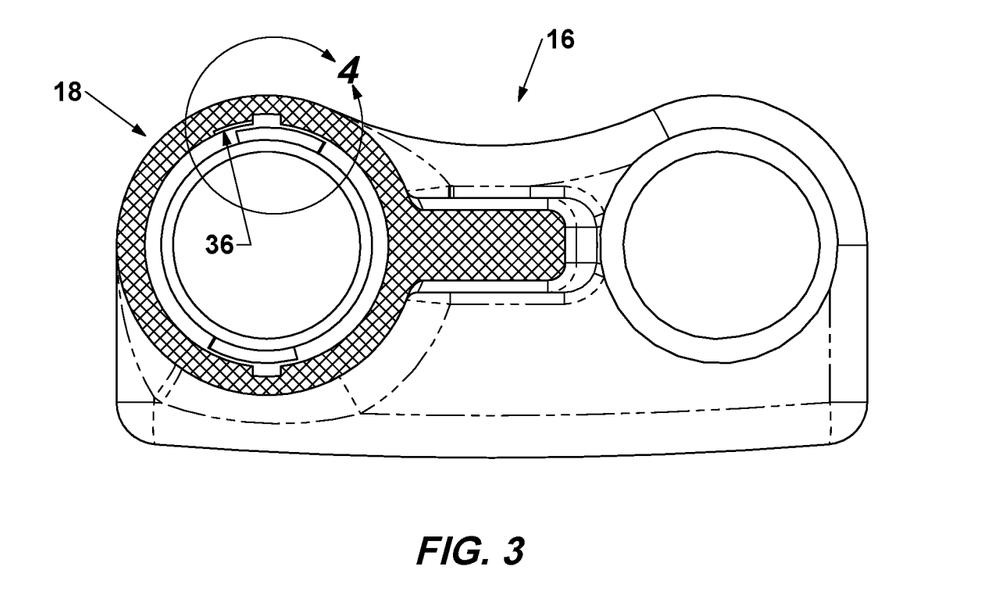
FIG. 3 is a plan view from along line 3-3 of FIG. 5 of the housing of FIG. 1.

FIG. 3 illustrates placement of sensor, or detector 36 along an inner surface of receiver 18 on housing 16. Although sensor 36 is shown as a single sensor, a pair of sensors can also be provided, one adjacent to where each spring arm locks to receiver 18. Although sensor 36 is shown mounted in a recess, sensor 36 can be integrally molded into a receiver, or carried within a wall inside of a slot, or laminated, adhesively affixed, secured with fasteners, or held with any other suitable structural affixation technique to a receiver of a housing, or to any related housing component. In one case, sensor 36 is a membrane switch provided in the receptacle. In another case, sensor 36 is a strain gage having a cylindrical segment contact surface configured to engage with a radially inwardly urged spring clip of the cap.

Figure 4:
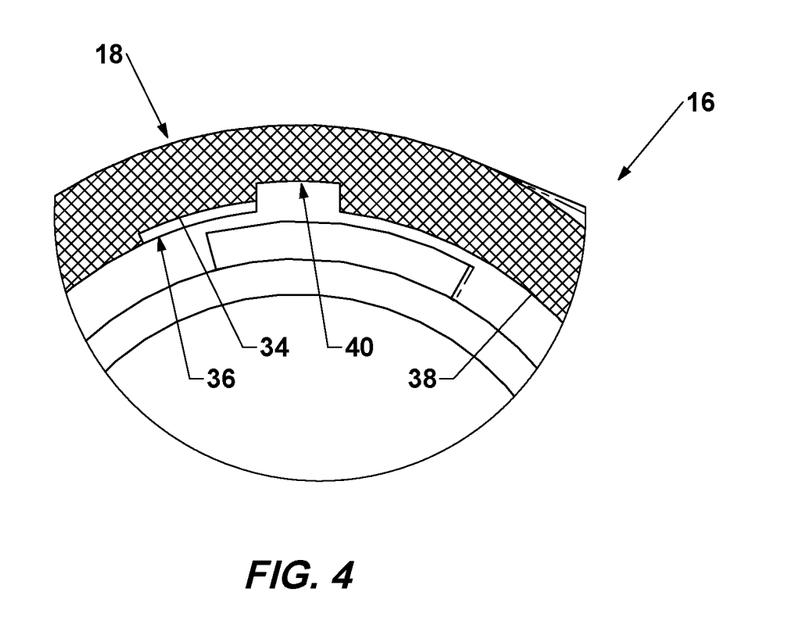
FIG. 4 is an enlarged view of the sensor in relation to the clip receiver used to detect attachment and removal of a cap and infusion line from the housing.

FIG. 4 shows placement of sensor 36 within recessed cavity 34 in receiver 38. A detent 40 is provided in front of sensor 36 configured to receive detent finger 42 on detent arm 26 of cap 14 (see FIG. 2) when cap 14 (see FIG. 2) is locked into receiver 18 of housing 16. As shown, sensor 36 is received in recess 34 so as to conform with an inner diameter surface 38 of receiver 18. When a cap is assembled within receiver 18, pressure, F, is applied across sensor 36 having a designed force, within a range, enabling identification of when a cap has been properly locked into place within receiver 18, as well as enabling detection of a non-complying or after-market cap being used in housing 16 due to a detected out-of-range force (or pressure) being detected by sensor 36.

Figure 5:
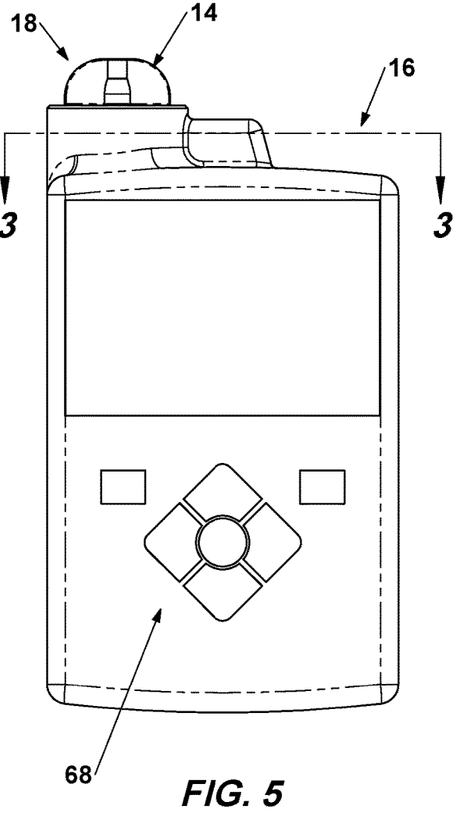
FIG. 5 is a front elevational view of the housing and infusion cap of FIG. 1 assembled together.
Figure 6:
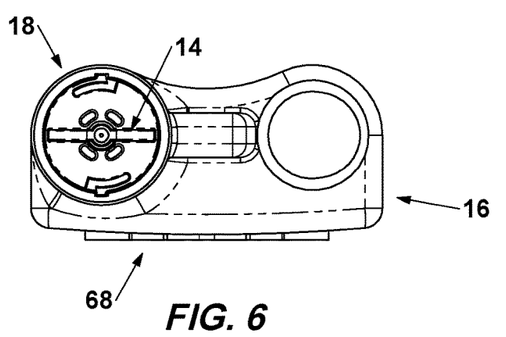
FIG. 6 is a plan view from above of the housing and infusion cap of FIG. 1.

Fluid delivery device 10 is shown in FIG. 5 having a front face with a user interface 68 provided on housing 16. Receiver 18 is integrally molded into housing 16 to removably receive insulin delivery cap 14. FIG. 6 shows cap 14 mated in locked relation with receiver 18.

Figure 7:
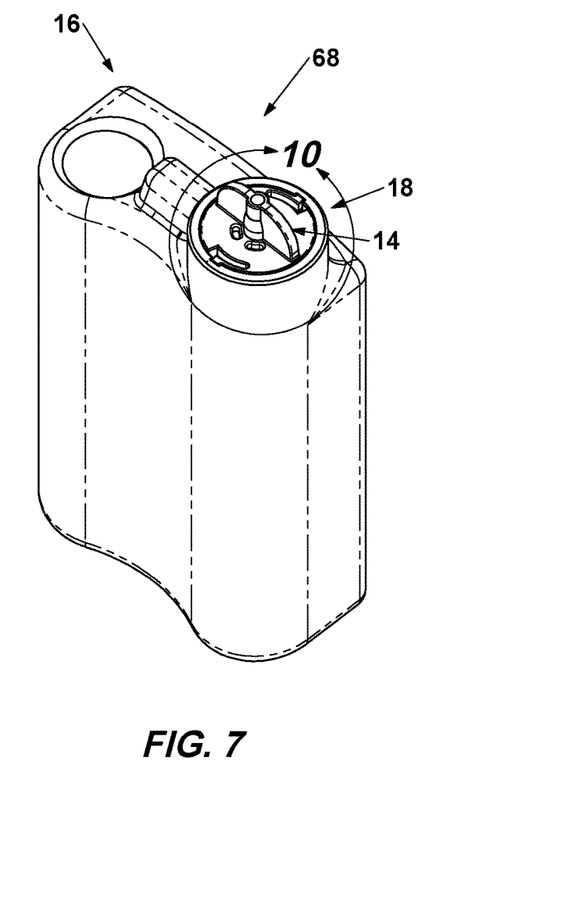
FIG. 7 is a perspective view from behind and above of the housing and infusion cap of FIG. 1 showing the cap being installed at selected stages of coupling to the housing shown further in sequential stages in FIGS. 8-10.
Figure 8:
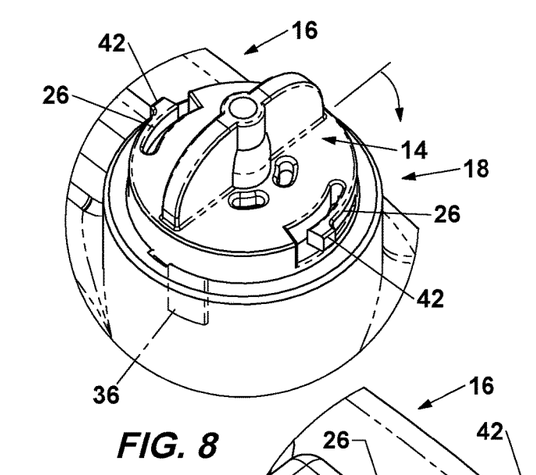
FIG. 8 is a partial perspective view from above taken within the same encircled region 10 of FIG. 7, but showing the cap just being inserted prior to rotary threaded engagement within the housing.
Figures 9, 10:
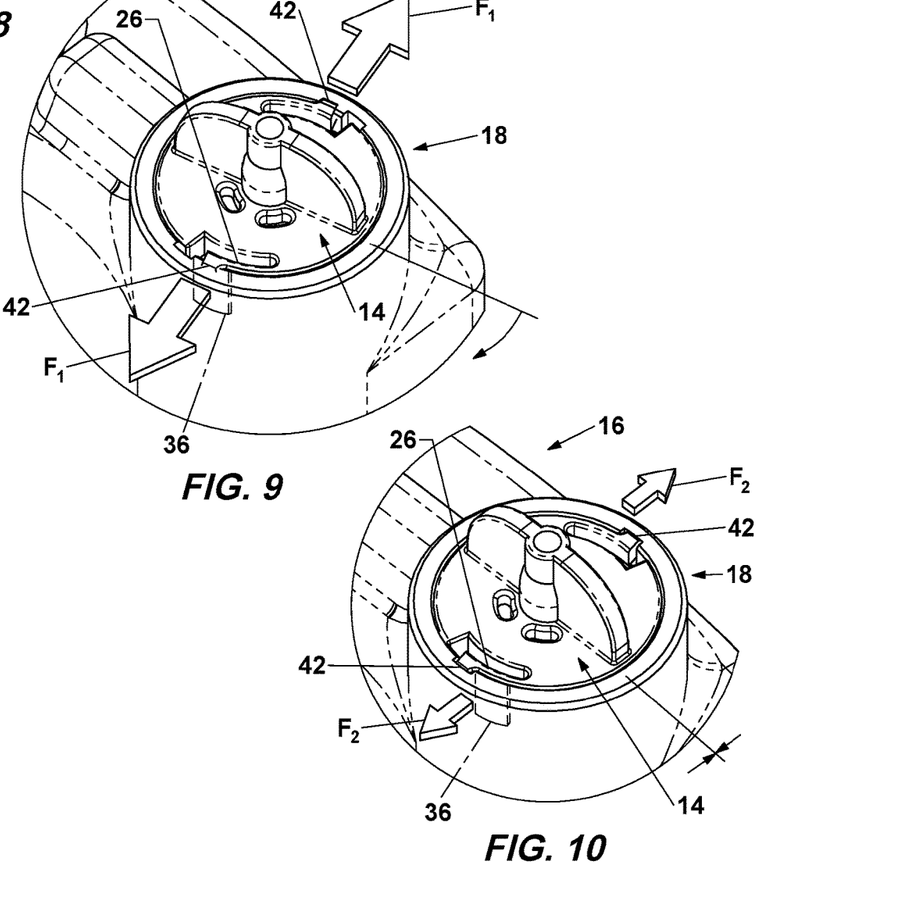
FIG. 9 is a partial perspective view from above taken within the same encircled region 10 of FIG. 7, but showing the cap partially rotated past the position shown in FIG. 8 with the spring arm engaging the sensor prior to locking within the housing.
FIG. 10 is a partial perspective view from above taken within encircled region 10 of FIG. 7 showing the cap fully threaded and locked into the receiver with the spring arm locked into the housing.

FIG. 7 is a perspective view from behind and above of the housing and infusion cap of FIG. 1 showing the cap being installed at selected stages of coupling to the housing shown further in sequential stages in FIGS. 8-10.

FIGS. 8-10 show cap 14 being threaded and locked into engagement with receiver 18 of housing 16 in three sequential moments in time corresponding with cap positions from FIG. 8 to FIG. 10.

FIG. 8 shows cap 14 being initially inserted into receiver 18 during an attachment and locking operation. Cap 14 is starting to initially thread into housing 16 at a rotary position nearly 90 degrees of rotation before one of the spring arms applies radial outward pressure to the sensor 36 at a fully closed and locked position (see FIG. 10).

FIG. 9 shows cap 14 and spring arm 26 partially rotated into threaded engagement with spring arm 26 engaging sensor 36. spring arm 26 applies detectable radial outward pressure, or force ($F_1$), to an inside surface of the receiver 16 just before cap 14 is locked into engagement within the receiver 18. More particularly, detent finger 42 of flexible detent arm 26 urges, or flexes arm 26 radially inwardly as cap 14 is being threaded into locked engagement with receiver 18 as finger 42 slides along wall 38.

FIG. 10 shows the cap 14 locked onto the receiver 18 with spring arm 26 locked into the housing 18. At this locked position, finger 42 is mated within detent, or slot 40 and a remaining arm portion of spring arm 26 is still outwardly against sensor 34 causing detectable pressure, or force ($F_2$), engagement there between. According to one construction, $F_2$ is less than $F_1$. Optionally, $F_1$ can equal force $F_2$, or $F_1$ can be less than $F_2$. For the cases where the two forces are not the same, the sensor board 60 (see FIG. 13) can be used to detect between two different status conditions of a cap on a receiver to monitor proper attachment and locking, and/or monitor compliance with usage, replacement, or source of goods.

Also shown in FIG. 10, a chamfered or tapered entry 35 into cylindrical wall 38 (see FIG. 2) and a chamfer, or taper on the bottom of each finger 42 serves to urges arms 26 radially inwardly as pressure is applied downwardly on cap 14 so that both fingers 42 clear inside diameter of wall 38, as shown in FIG. 7. Further rotation of cap 14 relative to receiver 18 causes each detent finger 42 to lock into a respective detent 40 on receiver 18, causing arm 26 to apply detected pressure or force to sensor 36 both prior to and while in a locked position. Such pressure levels can produce two distinct pressures that are detectable and recordable and can be used to detect if cap 14 is in a fully locked position.

Figure 11:
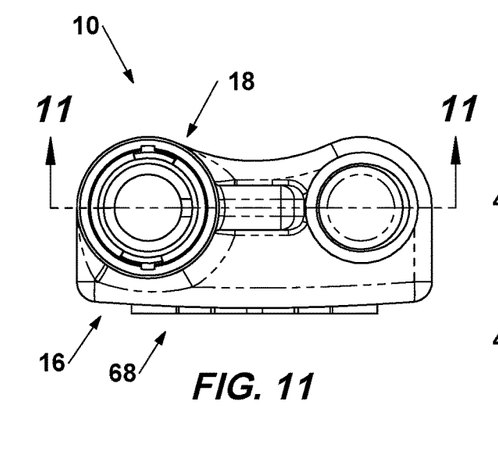
FIG. 11 is a plan view from above showing the housing and receiver without the cap.

FIG. 11 depicts housing 16 of infusion device 10 with the cap (not shown) removed from receiver 18. Receiver 18 provides a cylindrical receptacle, or bore into which a cap is axially inserted, rotated (in threaded engagement), and locked. The opposite steps are implemented to remove the cap from receiver 18 according to a consumable maintenance/replacement schedule, such as every 3 days.

Figure 12:
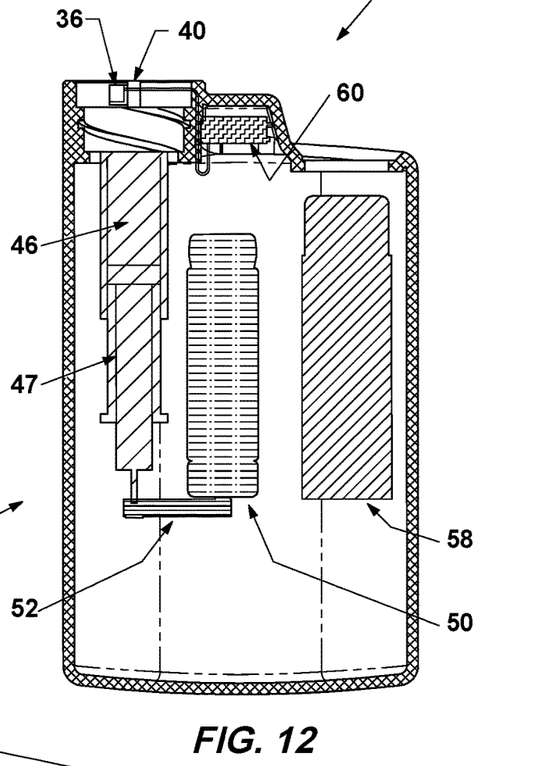
FIG. 12 is a simplified outline and internal front view of the infusion device of FIG. 1 showing internal operating components.

FIG. 12 shows further details of a cap sensing system 66 for detecting pressure exerted by a cap 14 when loaded onto a receiver 18 of a housing 16 for an infusion device 10. Cap 14 removably mates with a reservoir 46 coupled with a piston 48 that is driven by a motor 50 and motor control circuit board 52 using a battery, or power supply 58. A pressure point detection system printed circuit control board 60 is signal coupled to sensor 36 and includes processing circuitry, or a central processing unit 62 and memory 64 (see FIG. 10).

Figure 13:
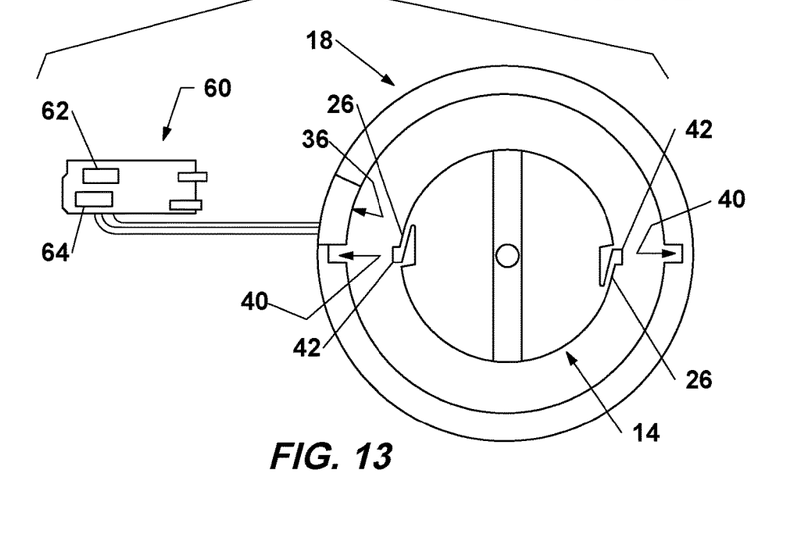
FIG. 13 is a simplified diagram of the sensing system, housing receptacle, and cap of FIG. 11.

FIG. 13 further details in simplified form the components of the cap sensing system 66. Cap 14 is shown with a reduced diameter relative to receiver 18 in order to help visualize interaction between the two components. Furthermore, such simplified depiction helps detail how cap 14 and receiver 18 cooperate to form a locking and sensing portion of an interlocking connection interface 12 (see FIG. 2). Pressure point detection system printed circuit control board 60 includes processing circuitry 62 and memory 64 that couple via conductive leads with sensor 36 on receiver 18. Opposed fingers 42 on detent arms 26 are urged radially outwardly until they both lock into respective detents 40 in receiver 18, while one of arms 26 creates outward pressure, or force against sensor 36 that is detected and stored in memory 64 on board 60.

The terms "a", "an", and "the" as used in the claims herein are used in conformance with long-standing claim drafting practice and not in a limiting way. Unless specifically set forth herein, the terms "a", "an", and "the" are not limited to one of such elements, but instead mean "at least one".

In compliance with the statute, the various embodiments have been described in language more or less specific as to structural and methodical features as the subject matter of this application was motivated in addressing detection of a cap being installed and removed from an insulin pump housing. It is to be understood, however, that the various embodiments are not limited to the specific features shown and described, since the means herein disclosed comprise disclosures of putting the various embodiments into effect. The various embodiments are, therefore, claimed in any of its forms or modifications within the proper scope of the appended claims appropriately interpreted in accordance with the doctrine of equivalents.

What is claimed is:

1. An apparatus for detecting releasable coupling of a cap from a fluid delivery device, comprising:
    a housing configured to carry a fluid delivery device having a reservoir of fluid:
    a receptacle provided by the housing having a coupling with an interface and a clip receiver having a cylindrical wall and an adjacent radial outwardly extending detent;
    an infusion cap coupled with a delivery tube and having a complementary coupling configured to engage with the interface of the coupling of the receptacle including a spring clip having a resilient arm and a terminal finger configured to interlock in urged engagement with the detent of the clip receiver during assembly; and
    a pressure sensor carried by the receptacle within the interface and configured to detect engagement pressures from the terminal finger of the spring clip with the receptacle during mating of the cap to the housing and de-mating of the cap from the housing and generate output signals having a known pressure value or a unique pressure range within a design range, the output signals indicative of a plurality of unique states of the cap engaged with the coupling of the receptacle, the plurality of unique states including a first state indicative of the finger engaged with the cylindrical wall of the clip receiver and a second state indicative of the finger engaged outwardly in locked relation into the detent of the clip receiver.

2. The apparatus of claim 1, wherein the interface of the receptacle includes a female threaded portion spaced axially of the clip receiver and a male interface on the cap includes a complementary male threaded portion.

3. The apparatus of claim 2, wherein the receptacle is a bore and the coupling of the receptacle includes a second clip receiver, wherein the clip receivers are radially opposed to one another, the sensor carried by one of the clip receivers.

4. The apparatus of claim 1, wherein the receptacle comprises a cylindrical bore and the clip receiver comprises a radially outwardly extending cylindrical recess segment and the sensor is affixed within the recess segment.

5. The apparatus of claim 4, wherein the sensor has a radially inwardly extending surface substantially conforming with an inner surface of the cylindrical bore of the receptacle.

6. The apparatus of claim 5, wherein the sensor is a strain gauge having a cylindrical segment contact surface configured to engage with the spring clip of the cap, wherein the spring clip is a radially inwardly urged spring clip.

7. The apparatus of claim 1, wherein the sensor comprises a membrane switch provided in the receptacle and the terminal finger is configured to urge the resilient arm radially inwardly when the cap is rotated relative to the receptacle while the terminal finger passes over the sensor.

8. The apparatus of claim 1, wherein the interface comprises a female threaded portion and the clip receiver is a radially outwardly extending recess provided in the interface.

9. The apparatus of claim 1, wherein engagement of the complementary coupling of the infusion cap with the coupling of the receptacle imparts a squeeze force on the spring clip detectable with the sensor.

10. The apparatus of claim 1, further comprising a pressure point detection system having processing circuitry and memory, configured to continuously detect a compliant state and a non-compliant state of the cap affixed to the interface of the coupling of the receptacle.

11. The apparatus of claim 1, wherein the sensor comprises a membrane switch configured to detect engagement pressure between the arm of the cap and the interface of the coupling of the receptacle to produce two distinct pressures indicative of a first pre-locked position and a second locked position.

12. The apparatus of claim 1, further comprising a pressure point detection system having processing circuitry and memory coupled with the sensor to receive a detected signal from the sensor having one of at least two distinct output levels.

13. The apparatus of claim 1, wherein the sensor is a strain gauge configured to generate the output signal.

14. The apparatus of claim 1, wherein the resilient arm of the spring clip comprises a detent arm.

15. The apparatus of claim 1, wherein the engagement pressure detected by the pressure sensor in the first state is greater than the engagement pressure detected by the pressure sensor in the second state.

16. The apparatus of claim 15, wherein the engagement pressure detected by the pressure sensor in the first state is different than the engagement pressure detected by the pressure sensor in the second state.

* * * * *